United States Patent [19]

Trepanier et al.

[11] 4,094,871

[45] June 13, 1978

[54] 1,3,4-BENZOTRIAZEPINE-2-THIONES

[75] Inventors: Donald L. Trepanier; Thomas C. Britton, both of Midland, Mich.

[73] Assignee: The Dow Chemical Company, Midland, Mich.

[21] Appl. No.: 769,126

[22] Filed: Feb. 16, 1977

[51] Int. Cl.² ................ C07D 255/04; C07D 413/06; C07D 401/06
[52] U.S. Cl. .................. 260/239.3 B; 260/239.3 T; 260/302 H; 548/324; 260/454; 260/552 SC; 424/244; 424/248.51; 424/270; 424/273 R; 260/243.3
[58] Field of Search ............................ 260/239.3 B

[56] References Cited

U.S. PATENT DOCUMENTS 3,176,008  3/1965  Sulkowski et al. ........... 260/239.3 B

OTHER PUBLICATIONS

Busch "Chem Berichte" Band 27 pp. 2897–2904 (1894).
Ishiwaka et al. "Bull. Chem. Soc. Japan" vol. 43 pp. 135–138 (1970).
Burger "Medicinal Chemistry" 2nd Ed. pp. 72–81 (1960) (Interscience).

*Primary Examiner*—Henry R. Jiles
*Assistant Examiner*—Robert T. Bond
*Attorney, Agent, or Firm*—James W. Ambrosius

[57] ABSTRACT

Novel 1,3,4-benzotriazepine-2-thiones and related tricyclic derivatives having central nervous system activity and a method of use for treating the symptoms of central nervous system depression and anxiety.

4 Claims, No Drawings

1,3,4-BENZOTRIAZEPINE-2-THIONES

BACKGROUND OF THE INVENTION

A number of methods for preparing 1,3,4-benzotriazepine-2-ones have been described in the literature. In general, the compounds are prepared by either of two methods from a 2-aminobenzophenone. In the first method the 2-aminobenzophenone is treated with semicarbazide to give an aminobenzophenone semicarbazone. This product is cyclized to give the benzotriazepine-2-one. See *Bull. Chem. Soc. Jap.* 43, 135–138 (1970); Japanese publications 70 11,148 (CA73:25544a) and 70 11,147 (CA73:25545b). Alternately, a 2-aminobenzophenone hydrazone is treated with phosgene to give the desired benzotriazepine-2-one. See U.S. Pat. No. 3,176,008; *J. Pharm. Sci.* 63(6), 838–41 (1974); and *J. Med. Chem.* 7(3) 386 (1964). Despite the reported central nervous system activity of the 1,3,4-benzotriazepine-2-ones, the thio analogues are unknown and no satisfactory method for their preparation has been described in the literature.

SUMMARY OF THE INVENTION

The present invention is directed to novel 1,3,4-benzotriazepine-2-thiones, related tricyclic derivatives and their method of use as psychoactive agents.

The benzotriazepine-2-thiones are represented by the general formula

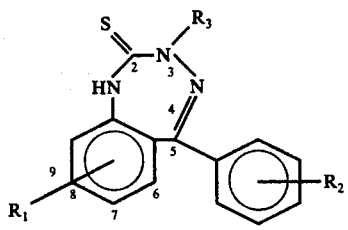

I wherein $R_1$ and $R_2$ independently represent hydrogen, a lower alkyl having from about 1 to 3 carbon atoms or halo; and $R_3$ represents a lower alkyl or substituted lower alkyl having from about 1 to 4 carbon atoms wherein the substitution is selected from the group comprising hydroxy, tertiary amino as for example diloweralkylamino, and a heterocyclic amine as for example morpholino and piperidino.

The related tricyclic compounds are represented by the general formula

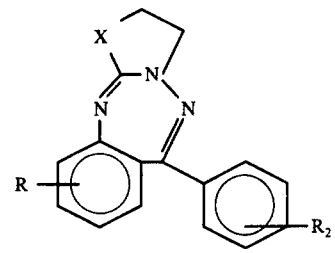

II wherein $R_1$ and $R_2$ are as defined above and X represents a sulfur atom or a secondary amine, i.e.

The compounds described above by the general formulas I and II have been shown to have central nervous system activity when administered internally to a mammal.

The invention also includes the pharmaceutically-acceptable salts of the benzotriazepine-2-thiones and tricyclic used in the practice of the present invention. As used in the specification and claims, the term "pharmaceutically-acceptable salts" refers to non-toxic acid addition salts of the compounds, the anions of which are relatively innocuous to animals at dosages consistent with good antidepressant activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

The benzotriazepine-2-thiones of the present invention are prepared by a novel process. In general, a 2-aminobenzophenone is reacted with thiophosgene to give the intermediate 2-benzoylphenylisothiocyanate. The intermediate is then treated with an alkylhydrazine or substituted alkylhydrazine to yield a 2-alkyl (or substituted alkyl)-4-(o-benzoylphenyl)-thiosemicarbazide. The thiosemicarbazide intermediate is cyclized to the desired 3-alkyl-2H-1,3,4-benzotriazepine-2-thione by heating briefly in acetic acid or n-propanol. The method of preparing compounds of the present invention may be summarized as follows:

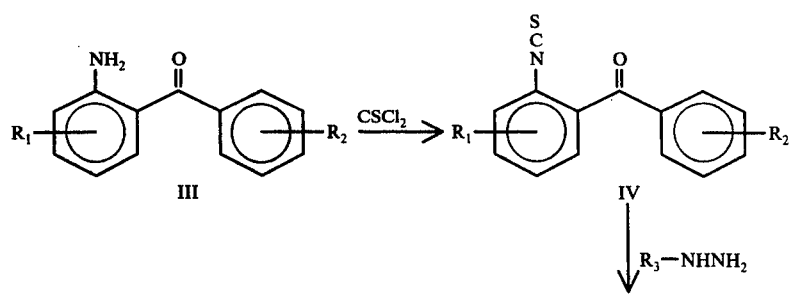

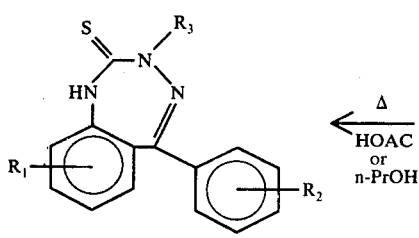 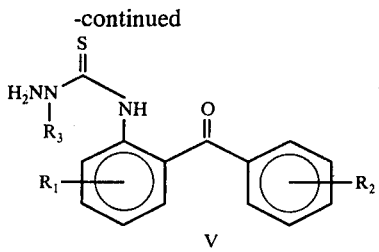

wherein $R_1$, $R_2$, and $R_3$ are the same as defined hereinbefore.

The tricyclic compounds of formula II are prepared in one of two ways depending upon the identity of X. Where X is a secondary amine, the compound is prepared by cyclizing 2-(b-aminoethyl)-thiosemicarbazide in acetic acid with heat. The reaction may be summarized as follows:

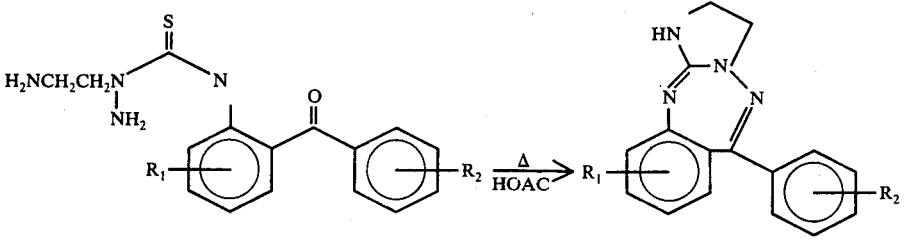

The sulfur isostere of the above tricyclic, i.e. where X is sulfur, is obtained from treatment of a 1,3,4-benzotriazepine-2-thione as in Formula I where $R_3$ is 2-hydroxyethyl with thionyl chloride followed by potassium carbonate. The reaction is summarized below.

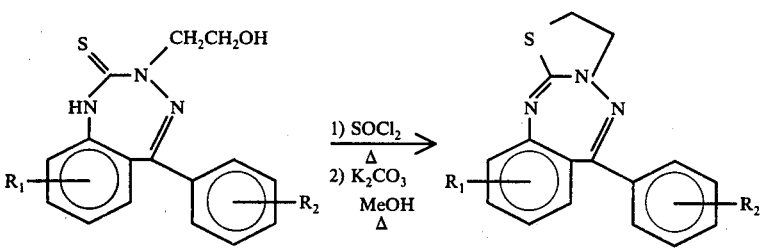

DETAILED DESCRIPTION OF THE INVENTION

The following examples further illustrate the present invention but are not to be construed as a limitation thereon.

EXAMPLE 1

Preparation of the intermediate 2-benzoyl-4-chlorophenylisothiocyanate

A two liter, 3-necked, round-bottom flask equipped with a condenser plus scrubber, mechanical stirrer and dropping funnel was used as the reaction vessel. The reaction vessel was cooled in an ice bath after charging with 600 ml of water. After the water had cooled, 63 ml (0.827 moles) of thiophosgene was added. The mixture was stirred vigorously while a solution containing 176 grams (0.760 moles) of 2-amino-5-chlorobenzophenone in about 0.5 liter of methylene chloride was added over a period of 20 to 25 minutes. After addition was complete, the funnel was rinsed with about 80 ml of methylene chloride and the reaction mixture was stirred for about one hour with the ice bath in place. Then the ice bath was removed and the reaction mixture was stirred for one additional hour. The organic and aqueous phases were separated, and the aqueous phase was extracted with methylene chloride. The extract was added to the organic phase, and combined material was dried with magnesium sulfate prior to concentration of the solvent in vacuo. The 2-benzoyl-4-chlorophenylisothiocyanate remained behind as a red oil which solidified on cooling. The product was recrystallized from hexane to leave a cream-colored solid having a melting point of 63°–65° C.

Elemental analysis indicated carbon 61.52%, hydrogen 2.76%, and nitrogen 4.90% compared to theoretical values of carbon 61.43%, hydrogen 2.95%, and nitrogen 5.12%.

Other intermediates of Formula IV above which exemplify those that can be employed to prepare compounds of the present invention and which were prepared using the general method described above are the following compounds:

2-benzoylphenylisothiocyanate
2-benzoyl-4-bromophenylisothiocyanate
2-benzoyl-4-methylphenylisothiocyanate
(5-chloro-2-isothiocyanatophenyl)(2-chlorophenyl)-methanone

EXAMPLE 2

Preparation of the intermediate N-(2-benzoyl-4-chlorophenyl)-methyl-hydrazinecarbothioamide A solution of 5.48 grams (0.02 mole) of 2-benzoyl-4-chlorophenylisothiocyanate in about 50 ml of ethyl ether was added dropwise to a solution containing 1.5 ml (0.028 mole) of methyl hydrazine (98%) in about 50 ml of ethyl ether cooled in an ice bath. Additional ethyl ether was added to facilitate stirring. Following addition of the isothiocyanate, the reaction mixture was stirred at room temperature for about 30 minutes. The solid was collected and washed with additional ethyl ether to yield 5.82 grams (91% yield) of N-(2-benzoyl-4-chlorophenyl)-methyl-hydrazinecarbothioamide as a white solid. The melting point was found to be 168.5°–170° C.

Elemental analysis found carbon 56.21%, hydrogen 4.60%, nitrogen 13.06%, and sulfur 9.98% compared to theoretical values of carbon 56.33%, hydrogen 4.41%, nitrogen 13.14%, and sulfur 10.03%.

In addition to the compound of Example 2 above, other 4-(o-benzoylphenyl)-thiosemicarbazide intermediates were prepared using the general procedure summarized above. Table I describes other compounds prepared which correspond to the general formula:

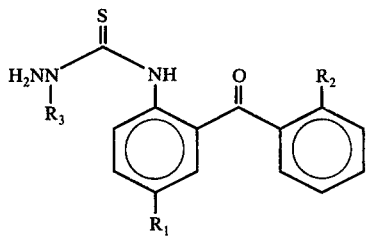

EXAMPLE 15

Preparation of 7-chloro-1,3-dihydro-3-methyl-5-phenyl-2H-1,3,4-benzotriazepine-2-thione A mixture containing 20.0 grams of N-(2-benzoyl-4-chlorophenyl)-methyl-hydrazine-carbothioamide (Example 2) in 250 ml of n-propanol was refluxed for about 2 hours. The yellow precipitate was cooled in an ice bath, and the resulting yellow precipitate was collected, washed with isopropanol and air dried to yield 7-chloro-1,3-dihydro-3-methyl-5-phenyl-2H-1,3,4-benzotriazepine-2-thione as a yellow solid. Additional product was obtained upon evaporation of the solvent under vacuum. The melting point was found to be 188–190° C.

Elemental analysis of the original precipitate yielded values of carbon 59.60%, hydrogen 3.75%, nitrogen 13.82%, and sulfur 10.65% as compared to theoretical values of carbon 59.69%, hydrogen 4.01%, nitrogen 13.92%, and sulfur 10.63%.

Other 2H-1,3,4-benzotriazepine-2-thiones were prepared using the general procedure explained above. Other compounds corresponding to the formula:

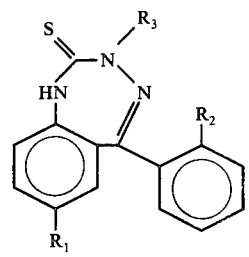

are shown in Table II.

TABLE I

| Intermediate Example No. | $R_1$ | $R_2$ | $R_3$ | M.p. (° C) | C | H | N | S |
|---|---|---|---|---|---|---|---|---|
| 3 | Cl | H | —(CH$_2$)$_2$—OH | 140–2 | 55.05 (54.93) | 4.41 (4.61) | 11.86 (12.01) | 9.30 (9.17) |
| 4 | Cl | H | —(CH$_2$)$_2$—N(CH$_3$)$_2$ | 136.5–138.5 | 57.30 (57.36) | 5.65 (5.62) | 14.86 (14.87) | 8.59 (8.51) |
| 5 | Cl | H | —(CH$_2$)$_3$—N(CH$_3$)$_2$ | 122–4 | 58.55 (58.37) | 5.87 (5.93) | 14.23 (14.33) | 8.33 (8.20) |
| 6 | Cl | H | —(CH$_2$)$_2$—N(morpholino) | 138.5–141 | 57.1 (57.34) | 5.53 (5.53) | 13.26 (13.37) | 7.48 (7.65) |
| 7 | Cl | H | —(CH$_2$)$_2$—N(piperidino) | 137–9 | 60.28 (60.49) | 5.99 (6.04) | 13.34 (13.44) | 7.70 (7.69) |
| 8 | Cl | H | —(CH$_2$)$_2$—N(C$_2$H$_5$)$_2$ | 108.5–109.5 | 59.3 (59.32) | 6.24 (6.22) | 13.83 (13.84) |  |
| 9 | Cl | H | —(CH$_2$)$_3$—N(C$_2$H$_5$)$_2$ | 155–116 | 60.0 (60.20) | 6.57 (6.50) | 13.53 (13.37) | 7.73 (7.65) |
| 10 | H | H | —(CH$_2$)$_3$—N(C$_2$H$_5$)$_2$ | 87–91 |  |  |  |  |
| 11 | Br | H | " | 107–9 | 54.0 (54.42) | 6.06 (5.87) | 12.10 (12.09) |  |
| 12 | CH$_3$ | H | " | 114–116 |  |  |  |  |
| 13 | Cl | Cl | " |  |  |  |  |  |
| 14 | Cl | H | —(CH$_2$)$_2$—NH$_2$ | 95.5–98 | 54.86 (55.09) | 4.90 (4.91) | 15.97 (16.06) | 9.29 (9.19) |

*Theoretical values are given in parenthesis.

TABLE II

| Compound Example No. | $R_1$ | $R_2$ | $R_3$ | M.p. (° C) | Recryst. Solvent | Analysis* C | H | N | S |
|---|---|---|---|---|---|---|---|---|---|
| 16 | Cl | H | —(CH$_2$)$_2$—OH | 151–3 | | 57.68 (57.91) | 4.24 (4.25) | 12.46 (12.66) | 9.38 (9.66) |
| 17 | Cl | H | —(CH$_2$)$_2$—N(CH$_3$)$_2$ | 173–5 dec | ethanol | 60.40 (60.24) | 5.47 (5.34) | 15.66 (15.61) | 8.72 (8.93) |
| 18 | Cl | H | —(CH$_2$)$_3$—N(CH$_3$)$_2$ | 117–119 | CH$_2$Cl$_2$/hexane | 61.35 (61.19) | 5.58 (5.68) | 14.96 (15.02) | 8.77 (8.60) |
| 19 | Cl | H | —(CH$_2$)$_2$—N⟨morpholino⟩ | 190–2 | isopropanol | 60.00 (59.91) | 5.23 (5.28) | 13.95 (13.98) | 8.00 (8.00) |
| 20 | Cl | H | —(CH$_2$)$_2$—N⟨piperidino⟩ | 131–3 | CH$_2$Cl$_2$/hexane | 63.14 (63.22) | 5.84 (5.81) | 14.09 (14.04) | 8.20 (8.04) |
| 21 | Cl | H | —(CH$_2$)$_2$—N(C$_2$H$_5$)$_2$ | 99–101 | hexane | 62.0 (62.08) | 5.94 (5.99) | 14.63 (14.48) | |
| 22 | Cl | H | —(CH$_2$)$_3$—N(C$_2$H$_5$)$_2$ | 92–4 | hexane | 63.2 (62.9) | 6.25 (6.28) | 13.97 (13.97) | |
| 23 | H | H | —(CH$_2$)$_3$—N(C$_2$H$_5$)$_2$ | 108–110 | hexane | 68.8 (68.81) | 7.20 (7.15) | 15.32 (15.29) | |
| 24 | Br | H | " | 107–9 | hexane | 56.3 (56.62) | 5.87 (5.66) | 12.71 (12.58) | |
| 25 | CH$_3$ | H | " | 101–3 | hexane | 69.5 (69.43) | 7.53 (7.42) | 14.79 (14.72) | |
| 26 | Cl | Cl | " | 102–103.5 | | 57.9 (57.93) | 5.46 (5.56) | 12.85 (12.87) | |

*Theoretical values are given in parenthesis.

EXAMPLE 27

Preparation of the tricyclic compound 8-chloro-2,3-dihydro-6-phenyl-thiazolo(2,3-b)(1,3,4)benzotriazepine A 15 gram quantity of 7-chloro-1,3-dihydro-3-(2-hydroxyethyl)-5-phenyl-2H-1,3,4-benzotriazepine-2-thione (Example 16) was slowly added with stirring over a 15–20 minute period to 100 ml of thionyl chloride. The reaction mixture was refluxed for about one hour after the addition was complete. The mixture was concentrated in vacuo in a rotary evaporator. The residue was slurried in benzene several times and evaporated to leave an orange solid which was washed with benzene and ethyl ether and air dried.

The material (13.1 grams) prepared above was dissolved in 300–400 ml of methanol to which about 30 grams of finely-ground anhydrous potassium carbonate was added. The reaction mixture was stirred and refluxed for about 15 minutes. The mixture was concentrated in vacuo on a rotary evaporator, and the residue was partitioned between chloroform and water. The chloroform phase was washed with water, dried with magnesium sulfate, and concentrated in vacuo to give a yellow oil which solidified on triturating with hexane. The 8-chloro-2,3-dihydro-6-phenyl-thiazolo(2,3-b)(1,3,4)benzotriazepine was washed with hexane and air dried. The product was recrystallized from isopropanol to yellow crystals with a melting point of 163°–165° C.

Elemental analysis found carbon 61.34%, hydrogen 3.86%, nitrogen 13.46% and sulfur 10.31% compared to theoretical values of carbon 61.24%, hydrogen 3.85%, nitrogen 13.39%, and sulfur 10.22%.

EXAMPLE 28

Preparation of the tricyclic compound 8-chloro-2,3-dihydro-6-phenyl-11H-imidazo(2,1-b)(1,3,4)benzotrizepine A mixture containing 10.0 grams of the intermediate 1-(2-aminoethyl)-N-(2-benzoyl-4-chlorophenyl)-hydrazinecarbothioamide (Example 14) and 200 ml of glacial acetic acid was refluxed for 30 minutes with stirring. The acetic acid was removed in vacuo to leave a yellow oil. The residue was dissolved in methylenechloride, washed with separate rinses of 10% sodium hydroxide and water, and dried with magnesium sulfate. The solvent was evaporated to leave the 8-chloro-2,3-dihydro-6-phenyl-11H-imidazo(2,1-b)(1,3,4)benzotriazepine. The product was recrystallized from isopropanol to yield yellow crystals having a melting point of 191.5° to 193.5° C. Infrared analysis was used to confirm the structure.

Elemental analysis showed carbon 64.71%, hydrogen 4.34%, chlorine 12.11% and nitrogen 18.73% compared to theoretical values of carbon 64.76%, hydrogen 4.42%, chlorine 11.95% and nitrogen 18.88%.

As noted above, the 1,3,4-benzotriazepine-2-thiones and related tricyclic compounds are active on the central nervous system when administered internally to a mammal in a psychoactively-effective amount. Member compounds have been found to be particularly useful as antidepressant/antianxiety agents when used in accordance with the present invention.

In practicing the method of the invention, one or more compounds of the present invention are administered internally to a mammal by a route effective to introduce an effective psychoactive amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood via the gastrointestinal tract. The compounds are orally effective, and generally have a higher ratio of toxic dose to effective dose when orally administered, and this route is preferred. The term psychoactive amount refers to the amount of the compound which is administered to the mammal to induce the desired central nervous system response. For example, an effective antidepressant or antianxiety amount is the amount sufficient to alleviate central nervous system depression or anxiety, respectively.

The psychoactive amount of the compound, that is, the amount of the compound sufficient to provide the desired effect, depends on various known factors such as the size, type, age and condition of the animal to be treated, the particular compound or compounds of the invention employed, the route and frequency of administration, the type and degree of central nervous system condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at a dosage rate of from 10 to about 150 mg/kg of bodyweight with about 20 to about 60 being preferred. Higher dosage rates may be employed, for example, when the compound is administered orally in a timed release dosage form. When administered by injection, good results are obtained with an amount of from about 10 to about 6 milligrams of the compound per kilogram of animal bodyweight. From about 20 to 150 milligrams of the active compound per kilogram, depending on dosage unit form employed, provide good results when the compound is administered orally. In the case of mammals suffering from central nervous system depression/anxiety (exhibiting symptoms of depression/anxiety), administration of an antidepressant/antianxiety amount of the compound is preferably repeated at predetermined intervals. It is generally desirable to administer the individual dosages at the lowest antidepressant/anxiety amount which provides the desired continuity consonant with a convenient dosing schedule. In a convenient repetitive procedure, the compounds are administered in single or divided oral doses at daily rates of about 20 to 150 milligrams per kilogram per day.

In practicing the method of the invention, the active ingredient is preferably incorporated in a composition comprising a pharmaceutical carrier and from about 0.001 to about 95 percent by weight of the compound. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa.(1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active compound can be formulated in conventional timed release capsule or tablet formulations.

Preferred compositions include sterile injectable solutions containing from about 0.001 to about 10 percent by weight of the compound in a pharmaceutical carrier suitable for injection, such as isotonic saline solution, Ringer's Injection USP, and lactated Ringer's USP, and the like.

EXAMPLE 29

A group of four mice were administered 60 mg/kg of the compound 7-chloro-3-(3-(diethylamino)propyl)-1,3-dihydro-5-phenyl-2H-1,3,4-benzotriazepine-2-thione (Example 22) by intraperitoneal injection via an aqueous carrier. A similar group of mice serving as controls were injected only with the carrier. After 30 minutes, both groups of mice were injected subcutaneously with 2.5 mg/kg of reserpine. The administration of reserpine to the control mice resulted in a classical progression of symptoms beginning with a dropping of the eyelids (ptosis) and later culminating in a generalized depression with decreased spontaneous motor activity and decreased responsiveness to auditary and tacticle stimuli.

Animals injected with the benzotriazepine compound were graded after 45 minutes on the following basis: no ptosis = 0, partial ptosis = 1, complete ptosis = 2. Adding the grades for the four test mice gave a value of 3 out of a possible 8 or 83% protection against reserpine-induced ptosis. The value for the four control mice was 8.

EXAMPLE 30

Antidepressant activity may also be illustrated in vitro by measuring the uptake of the neurotransmittors norepinephrine and serotonin in synaptosome preparations prepared from the forebrains of rats. The synaptosome preparation is incubated at 37° C with radioactive neurotransmittor and the test compound at a concentration of 10 $\mu$g/ml. the synaptosomes are isolated and the uptake of labelled neurotransmittor measured by liquid scintillation spectrometry using standard techniques. Percent relative uptake is determined by comparing the radioactivity taken in the test synaptosome preparation with that of a similarly incubated saline control. Using this technique the compound 7-chloro-3-(diethylamino)propyl)-1,3-dihydro-5-phenyl-2H-1,3,4-benzotriazepine-2-thione (Example 22) showed 8% relative uptake of norepinephrine and 9% relative uptake of seratonin.

Other compounds of the present invention while generally less active than the compound of Example 19 also showed significant inhibition of neurotransmittor uptake under the condition of this test.

EXAMPLE 31

Effective antidepressants have been found to potentiate the uptake of d-amphetamine into the central nervous system. The compound 7-chloro-3-(3-(diethylamino)propyl)-1,3-dihydro-5-phenyl-2H-1,3,4-benzotriazepine-2-thione (Example 22) was administered at a dosage of 20 mg/kg to male rats 60 minutes prior to intraperitoneal administration of radioactive labelled d-amphetamine. Two hours after amphetamine administration, the animals were sacrificed and the forebrains tested for the presence of labelled amphetamine. Values are given as a ratio of labelled amphetamine in the rats pretreated with the benzotriazepine compound to the amount of labelled amphetamine in the forebrain of similarly treated control animals. Therefore, values above 1.0 indicate activity. The benzotriazepine-2-thione had a value of 3.1 when given orally and 3.7 when given intraperitoneally.

EXAMPLE 32

Compounds exhibiting antianxiety properties block the stress induced rise of serum corticosteroid levels. See *British Medical Journal,* 1971(2), p. 310–313. Corticosteroid levels were compared between stressed male rats pretreated with 10 mg/kg given by intraperitoneal injection to corticosteroid levels of stressed male rats pretreated with saline. The results were expressed as a ratio with values less than 1.0 indicative of activity. The compound 7-chloro-1,3-dihydro-3-(2-(4-morpholinyl)ethyl)-5-phenyl-2H-1,3,4-benzotriazepine-2-thione (Example 19) gave a value of 0.13. Other compounds described within the scope of the present invention, although generally less active, also showed significant antianxiety properties when used in the above test.

What is claimed is:

1. A compound having the formula

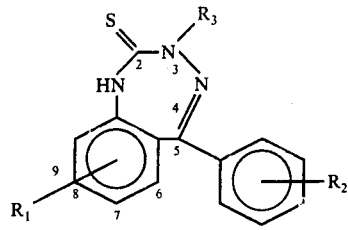

wherein $R_1$ and $R_2$ independently represent hydrogen, lower alkyl, or halo and $R_3$ represents a lower alkyl or substituted lower alkyl wherein the substitution is selected from the group comprising hydroxy, morpholino, piperidino, dimethylamino, or diethylamino and further including the pharmaceutically-acceptable salts thereof.

2. The compound of claim 1 wherein $R_1$ is substituted onto the 7 position and $R_2$ is hydrogen.

3. The compound of claim 2 which is 7-chloro-3-(3-(diethylamino)propyl)-1,3-dihydro-5-phenyl-2H-1,3,4-benzotriazepine-2-thione.

4. The compound of claim 2 which is 7-chloro-1,3-dihydro-3-(2-(4-morpholinyl)ethyl)-5-phenyl-2H-1,3,4-benzotriazepine-2-thione.

* * * * *

UNITED STATES PATENT AND TRADEMARK OFFICE
CERTIFICATE OF CORRECTION

PATENT NO. : 4,094,871

DATED : June 13, 1978

INVENTOR(S) : Donald L. Trepanier, et al.

It is certified that error appears in the above-identified patent and that said Letters Patent are hereby corrected as shown below:

Column 6, line 17, omit comma after "hydrogen";

Columns 5 and 6 "TABLE I", Column heading "R2" should read -- $R_2$ --;

Columns 5 and 6 "TABLE I", Example 6 under column heading "N", "(13.37" should read -- (13.37) --;

Columns 5 and 6 "TABLE I", Example 6 under column heading "S", center "(7.65)" properly;

Columns 5 and 6 "TABLE I", Example 9 under column heading "M.p.(°C), "155-116" should read -- 115-116 --;

Column 7, line 66 "benzotrizepine" should read -- benzotriazepine --;

Column 9, line 17 "from 10" should read -- from about 10 --;

Column 10, line 22 "83%" should read -- 63% --;

Column 10, line 34 "the" should be capitalized and begin a new sentence;

Column 10, line 48 "condition" should read -- conditions --;

UNITED STATES PATENT AND TRADEMARK OFFICE
CERTIFICATE OF CORRECTION

PATENT NO. : 4,094,871

DATED : June 13, 1978

INVENTOR(S) : Donald L. Trepanier, et al.

It is certified that error appears in the above-identified patent and that said Letters Patent are hereby corrected as shown below:

Column 12, lines 1 - 10, "Formula" should read as follows:

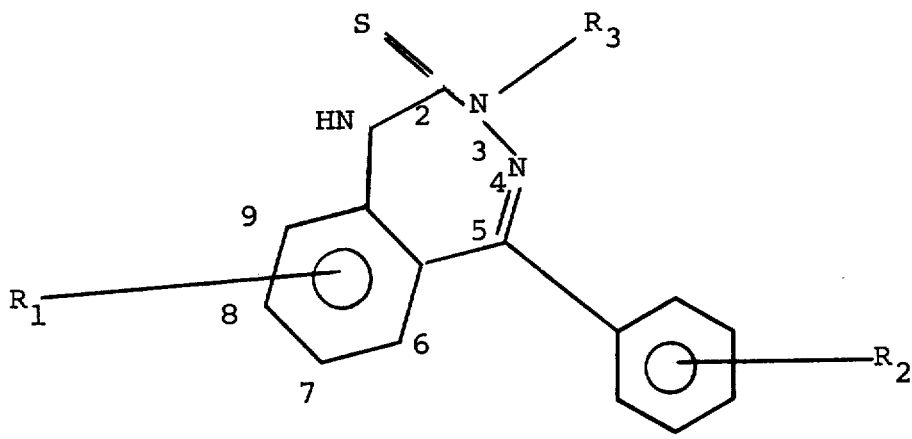

Signed and Sealed this

Nineteenth Day of December 1978

[SEAL]

Attest:

RUTH C. MASON
*Attesting Officer*

DONALD W. BANNER
*Commissioner of Patents and Trademarks*